(12) United States Patent
Kohler Riedi et al.

(10) Patent No.: US 12,702,593 B2
(45) Date of Patent: Aug. 11, 2026

(54) REINFORCED FIBER WEB AND WOUND DRESSING MATERIAL INCLUDING THE SAME

(71) Applicant: Solventum Intellectual Properties Company, Maplewood, MN (US)

(72) Inventors: Petra L. Kohler Riedi, Minneapolis, MN (US); Saurabh Batra, Minneapolis, MN (US); Joseph J. Stoffel, Hastings, MN (US); Rajan B. Bodkhe, Woodbury, MN (US); Joseph A. Dunbar, Woodbury, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 210 days.

(21) Appl. No.: 18/275,271

(22) PCT Filed: Jan. 27, 2022

(86) PCT No.: PCT/IB2022/050725

§ 371 (c)(1), (2) Date: Aug. 1, 2023

(87) PCT Pub. No.: WO2022/162581

PCT Pub. Date: Aug. 4, 2022

(65) Prior Publication Data

US 2024/0115427 A1 Apr. 11, 2024

Related U.S. Application Data

(60) Provisional application No. 63/144,044, filed on Feb. 1, 2021.

(51) Int. Cl.

*A61F 13/00* (2006.01)
*A61F 13/0246* (2024.01)

(Continued)

(52) U.S. Cl.

CPC .... *A61F 13/00063* (2013.01); *A61F 13/0246* (2013.01); *A61L 15/225* (2013.01); *A61L 15/44* (2013.01); *A61L 2300/404* (2013.01)

(58) Field of Classification Search

None

See application file for complete search history.

(56) References Cited

U.S. PATENT DOCUMENTS 3,683,921 A 8/1972 Brook et al.
3,849,241 A 11/1974 Butin et al.

(Continued)

FOREIGN PATENT DOCUMENTS

CN 202626547 U * 12/2012
CN 106729930 A 5/2017

(Continued)

OTHER PUBLICATIONS

CN 202626547 U Translation (Year: 2012).*

(Continued)

*Primary Examiner* — Kim M Lewis

(57) ABSTRACT

A reinforced fiber web has first and second opposed major sides and comprises first and second fiber webs having a reinforcing mesh disposed therebetween. The first and second fiber webs are physically entangled with each other and the reinforcing mesh. A wound dressing material comprises the reinforced fiber web, a first wound-contact scrim, and a first antimicrobial layer sandwiched therebetween. The first wound-contact scrim comprises water-sensitive fibers comprising a copolymer comprising divalent hydroxyethylene monomer units and divalent dihydroxybutylene monomer units.

20 Claims, 1 Drawing Sheet

(51) Int. Cl.
*A61L 15/22* (2006.01)
*A61L 15/44* (2006.01)

(56) References Cited

U.S. PATENT DOCUMENTS

| | | | | |
|---|---|---|---|---|
| 4,118,531 | A | 10/1978 | Hauser | |
| 4,307,143 | A | 12/1981 | Meitner | |
| 4,707,398 | A | 11/1987 | Boggs | |
| 4,921,704 | A | 5/1990 | Fabo | |
| 5,207,790 | A | 5/1993 | Eveillard | |
| 5,207,970 | A | 5/1993 | Joseph et al. | |
| 5,232,770 | A | 8/1993 | Joseph | |
| 5,238,733 | A | 8/1993 | Joseph et al. | |
| 5,258,220 | A | 11/1993 | Joseph | |
| 5,334,446 | A | 8/1994 | Quantrille et al. | |
| 5,698,322 | A | 12/1997 | Tsai et al. | |
| 5,951,993 | A | 9/1999 | Scholz et al. | |
| 6,105,400 | A * | 8/2000 | Yoon | D04B 21/02 66/194 |
| 6,268,544 | B1 | 7/2001 | Court et al. | |
| 6,494,974 | B2 | 12/2002 | Riddell | |
| 6,534,083 | B2 | 3/2003 | Gilding et al. | |
| 6,735,832 | B1 | 5/2004 | Putnam et al. | |
| 6,872,311 | B2 | 3/2005 | Koslow | |
| 7,008,207 | B2 | 3/2006 | Bansal et al. | |
| 7,210,206 | B2 | 5/2007 | Ferguson | |
| 7,652,189 | B2 | 1/2010 | Bray | |
| 7,745,681 | B1 | 6/2010 | Ferguson | |
| 7,745,687 | B2 | 6/2010 | Heyn et al. | |
| 8,844,158 | B2 | 9/2014 | Dehn | |
| 8,926,877 | B2 | 1/2015 | Melik et al. | |
| 9,326,894 | B2 | 5/2016 | Gladman et al. | |
| 9,408,942 | B2 | 8/2016 | Röttger et al. | |
| 10,342,707 | B2 | 7/2019 | Wang et al. | |
| 10,350,326 | B2 | 7/2019 | Bonnefin et al. | |
| 10,500,300 | B2 | 12/2019 | Dybe et al. | |
| 2005/0266760 | A1 | 12/2005 | Chhabra et al. | |
| 2005/0287891 | A1 | 12/2005 | Park | |
| 2006/0096911 | A1 | 5/2006 | Brey et al. | |
| 2006/0211972 | A1 | 9/2006 | Nielsen et al. | |
| 2009/0287130 | A1 | 11/2009 | Lee et al. | |
| 2010/0129633 | A1 | 5/2010 | Law | |
| 2011/0184365 | A1 | 7/2011 | Röttger et al. | |
| 2011/0247839 | A1 | 10/2011 | Lalouch et al. | |
| 2016/0287743 | A1 | 10/2016 | Andrews | |
| 2018/0028363 | A1 | 2/2018 | Hoggarth et al. | |
| 2018/0214598 | A1* | 8/2018 | Stasko | A61L 15/425 |
| 2019/0021912 | A1 | 1/2019 | Cotton et al. | |
| 2019/0351092 | A1 | 11/2019 | Silver et al. | |
| 2020/0000642 | A1 | 1/2020 | Waite | |
| 2020/0016292 | A1 | 1/2020 | Holscher et al. | |
| 2020/0155361 | A1 | 5/2020 | Pigg et al. | |
| 2020/0163803 | A1 | 5/2020 | Pigg et al. | |

FOREIGN PATENT DOCUMENTS

| | | | | |
|---|---|---|---|---|
| EP | 0467409 | A1 * | 1/1992 | A61F 13/539 |
| EP | 3087960 | A1 | 11/2016 | |
| WO | 1999067456 | A1 | 12/1999 | |
| WO | 2003033041 | A2 | 4/2003 | |
| WO | 2016141892 | A1 | 9/2016 | |
| WO | 2019011000 | A1 | 1/2019 | |
| WO | 2019083563 | A1 | 5/2019 | |
| WO | 2020261035 | A1 | 12/2020 | |
| WO | WO-2021059188 | A1 * | 4/2021 | A61F 13/00063 |
| WO | 2021084354 | A1 | 5/2021 | |
| WO | 2021250513 | A1 | 12/2021 | |
| WO | 2022064291 | A1 | 3/2022 | |
| WO | 2022162581 | A1 | 8/2022 | |

OTHER PUBLICATIONS

"Aquacel® Ag Extra", Convatec Inc., 2022, [Online], [Retrieved from internet on Sep. 26, 2023], URL: <https://www.convatec.com/wound-skin/aquacel-dressings/aquacel-ag-extra/>, 10 pages.

"Modified Cellulose Dressings", SFM Limited, [Online], [Retrieved from internet on Sep. 26, 2023], URL: (https://www.sfm-limited.com/product/modified-cellulose/), (date unknown but believed to be prior to the date of the filing of the present application), 6 pages.

International Search Report for PCT International Application No. PCT/IB2022/050725, mailed on Apr. 14, 2022, 4 pages.

Wente, "Superfine Thermoplastic Fibers", Industrial and Engineering Chemistry, Aug. 1956, vol. 48, No. 8, pp. 1342-1346.

* cited by examiner 100
130
104
120
102
110

210a
200
220
210b 300
320a
330a
102
100
104
330b
320b 400
102
420a
430a
460
100
460
104
440

REINFORCED FIBER WEB AND WOUND DRESSING MATERIAL INCLUDING THE SAME

CROSS REFERENCE TO RELATED APPLICATIONS

This application is a national stage filing under 35 U.S.C. 371 of PCT/IB2022/050725, filed Jan. 27, 2022, which claims the benefit of U.S. Provisional Application No. 63/144,044, filed Feb. 1, 2021, the disclosures of which are incorporated by reference in their entirety herein.

BACKGROUND

Traditionally, wet-to-dry gauze has been used to dress wounds. Dressings that create and maintain a moist environment, however, are now typically considered to provide optimal conditions for wound healing. Indeed, highly hydrophilic and absorbent wound dressing materials are part of the rapidly growing advanced wound care market. High-gelling fiber wound dressing products are popular with clinicians and are made of materials which absorb and hold moisture to create a gel-like environment to maintain moisture at the wound site. The most common materials used in these products are alginate and carboxymethyl cellulose.

Many wound care products include cationic antiseptics, which kill a wide variety of microorganisms, but are sequestered and/or deactivated by anionic materials such as alginate and carboxymethyl cellulose in the wound care product itself. Rayon is another highly hydrophilic material often used in wound care products, but it likewise also binds cationic antimicrobial molecules.

There is a continuing need for materials and articles to facilitate wound healing.

SUMMARY

The present disclosure provides materials and articles useful for the manufacture of absorbent wound dressings, and especially absorbent wound dressings having good strength and handling characteristics.

In a first aspect, the present disclosure provides a reinforced fiber web having first and second opposed major sides, wherein the reinforced fiber web comprises first and second fiber webs having a reinforcing mesh disposed therebetween, wherein the wherein the first and second fiber webs are physically entangled with each other and the reinforcing mesh, and wherein at least one of the first and second fiber webs comprises water-sensitive fibers comprising hydrophilic aliphatic thermoplastic polyurethane.

In a second aspect, the present disclosure provides a wound dressing material comprising:

- a reinforced fiber web having first and second opposed major sides, wherein the reinforced fiber web comprises first and second fiber webs having a reinforcing mesh disposed therebetween, and wherein the first and second fiber webs are physically entangled with each other and the reinforcing mesh;
- a first wound-contact scrim comprising first water-sensitive fibers, wherein the first water-sensitive fibers comprise a first copolymer comprising divalent hydroxyethylene monomer units and divalent dihydroxybutylene monomer units; and
- a first antimicrobial layer sandwiched between the first major side of the reinforced fiber web and the first wound-contact scrim.

As used herein:

- the term "sandwiched between" means disposed between and contacting;
- the term "scrim" refers to a lightweight highly porous fabric that may be woven or nonwoven;
- the term "water-sensitive" means water swellable and/or water-soluble;
- the term "wound" refers to an injury to a subject (e.g., a mammal) which involves a break in the normal skin barrier exposing tissue below, which is caused by, for example, lacerations, surgery, burns, damage to underlying tissue such as pressure sores, or poor circulation. Wounds are understood to include both acute and chronic wounds; and.
- the term "wound contact" means suitable for contact with a wound; however, other uses are also contemplated and are included within the meaning of the term.

Features and advantages of the present disclosure will be further understood upon consideration of the detailed description as well as the appended claims.

Figures 1, 2, 3, 4:
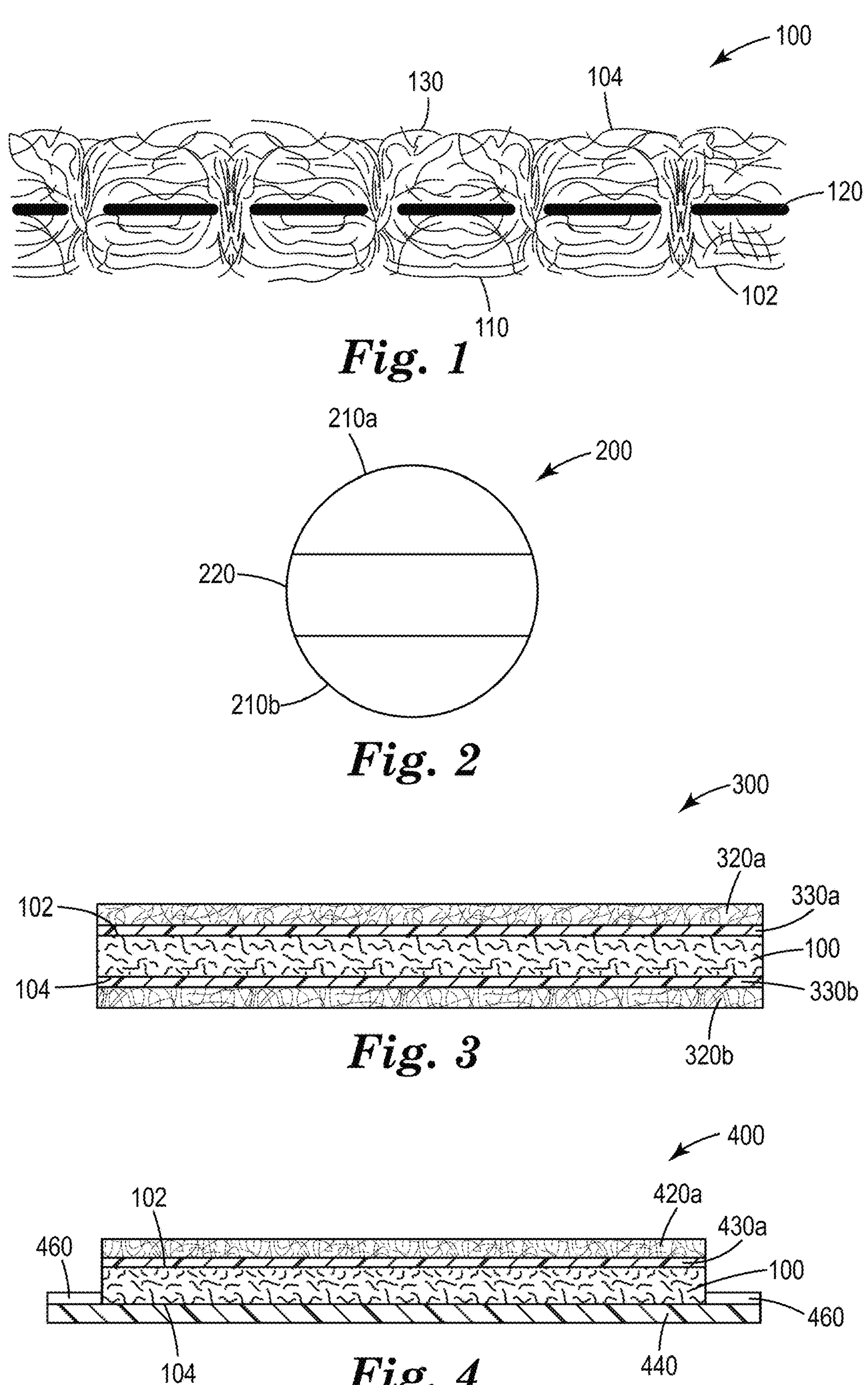
FIG. 1 is a schematic side view of an exemplary reinforced fiber web 100 according to the present disclosure.
FIG. 2 is a schematic axial view of an exemplary multilayer fiber 200 according to the present disclosure.
FIG. 3 is a schematic side view of an exemplary wound dressing material 300 according to the present disclosure.
FIG. 4 is a schematic side view of another exemplary wound dressing material 400 according to the present disclosure.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

FIG. 1 shows an exemplary reinforced fiber web 100 according to the present disclosure. Reinforced fiber web 100 has first and second opposed major sides (102,104). Reinforced fiber web 100 comprises first and second fiber webs (110, 130) with reinforcing mesh 120 disposed therebetween. First and second fiber webs (110, 130) are physically entangled with each other and reinforcing mesh 120. At least one of the first and second fiber webs comprises water-sensitive fibers comprising hydrophilic aliphatic thermoplastic polyurethane.

The reinforcing mesh (e.g., a net) may comprise a unitary polymer mesh, or a fabric, and has openings extending therethough. In some embodiments, the openings are arranged to form a regular array, although this is not a requirement. The openings may be of similar or different shapes and/or sizes. Exemplary fabrics include nonwovens (e.g., spunbond, meltbown, carded, air-laid, spunlaced fabrics), wovens, and knits. Knit fabrics and unitary films are typically preferred in some embodiments.

The openings preferably account for at least 5 percent, at least 10 percent, at least 20 percent, at least 30 percent, at least 40 percent, at least 50 percent, at least 60 percent, at least at least 70 percent, or even at least 80 percent of the surface area of the reinforcing mesh.

The reinforcing mesh contributes structural integrity to the reinforced fiber web.

In some embodiments, the reinforcing mesh may have a basis weight of 10 to 100 grams per square meter (gsm), preferably 30 to 85 gsm, and more preferably 50 to 70 gsm, although other basis weights may also be used.

Exemplary suitable materials for the reinforcing mesh include polyesters, polyamides, polyolefins, polycarbonates, polyimides, acrylics, polystyrene, polyurethanes, and combinations thereof, although other materials may also be used.

The first and second fiber webs of the reinforcing web may be the same or different (e.g., with respect to composition and/or construction).

In some embodiments, for example, where resistance to exudate and/or water swellability/solubility is desired, the first and/or second fiber webs may comprise fibers comprising polyolefin(s) (e.g., polyethylene (HDPE, LDPE, LLDPE, VLDPE; ULDPE, UHMW-PE, polypropylene, polybutylene, poly(l-butene), polyisobutylene, poly(l-pentene), poly(4-methylpent-1-ene), polybutadiene, or polyisoprene), polyester(s) (e.g., polylactic acid, polybutylene terephthalate, and polyethylene terephthalate), polyvinyl chloride, polymethyl methacrylate, polyacrylonitrile and copolymer(s) of acrylonitrile, polyamide(s) (e.g., polycaprolactam or nylon 6,6), polystyrene(s), polyphenylene sulfide(s), polysulfone(s), polyoxymethylene(s), polyimide(s), polyurea(s), hydrophobic thermoplastic polyurethane(s), styrenic block copolymer(s) (e.g., styrene-isoprene-styrene (SIS) block copolymers, styrene-ethylene-butadiene-styrene (SEBS) block copolymers, or styrene-butadiene-styrene (SBS) block copolymers), metal (e.g., stainless steel, nickel, tin, silver, copper, or aluminum fibers), glass fibers, ceramic fibers, natural fiber(s) (e.g., cotton fibers, wool fibers, cashmere fibers, kenaf fibers, jute fibers, flax fibers, hemp fibers, cellulosic fibers, sisal fibers, coir fibers), or any combination thereof.

In some embodiments, for example, where solubility and/or swellability in exudate and/or water is desired, the first and/or second fiber webs may comprise fibers comprising polyvinyl alcohol(s), carboxymethyl cellulose, rayon, cotton, cellulose acetate, hydrophilic thermoplastic polyurethane(s), chitosan, polyacrylic acid, sulfonated cellulose, cellulose ethyl sulfonate, alginate, or any combination thereof.

In some embodiments, the first and/or second fiber webs may comprise multi-component fibers. Referring now to FIG. 2, exemplary multi-component fiber 200 comprises a first phase 210*a*, 210*b* and a second phase 220. First phases 210*a*, 210*b* comprise a thermoplastic polymer that is not water-sensitive. Examples include polyolefins such as polyethylenes (e.g., HDPE, LDPE, LLDPE, VLDPE; ULDPE, UHMW-PE grades), polypropylenes, polybutylenes, poly (ether ether ketone), and poly-4-methyl-pentenes), certain polyesters (e.g., polyethylene terephthalate), polyvinyl chloride, certain acrylic polymers (e.g., polymethyl methacrylate, polyacrylonitrile), certain polyamides, polystyrene, styrenic block copolymers (e.g., SIS, SEBS, SBS), polysulfones, and certain polyurethanes.

Second phase 220 comprises a water-sensitive thermoplastic polymer. Exemplary water-sensitive thermoplastic polymers include ethylene-vinyl alcohol copolymers, certain partially hydrolyzed polyvinyl acetates (e.g., polyvinyl alcohol(s)), carboxymethyl cellulose, cellulose acetate, hydrophilic thermoplastic polyurethane(s), highly amorphous polyvinyl alcohols having divalent monomer units of hydroxyethylene, 3,4-dihydroxybutan-1,2-diyl, and optionally acetoxyethylene, or a combination thereof. Either of both of the first and second phases may be continuous of discontinuous. Of these, hydrophilic thermoplastic polyurethanes are preferred in some embodiments.

While the multi-component fiber 200 shown in FIG. 2 has a circular cross-section, other cross-sections may also be used such as, for example, triangular, square, rectangular, pentagonal, hexagonal, heptagonal, octagonal, star-shaped, oval, trilobal, and tetralobal. Likewise, while FIG. 2 shows a 3-layer fiber, other configurations not shown may also be used. For example, a core-sheath construction wherein water-sensitive thermoplastic polymer is included in the sheath and a thermoplastic polymer that is not water-sensitive is included in the fiber core may be desirable in some circumstances.

Multi-component fibers can be made by well-known coextrusion techniques. For example, details concerning multi-component fiber manufacturing extrusion techniques can be found in U.S. Pat. Nos. 5,207,790 and 5,232,770 (Joseph et al.), the disclosures of which are incorporated herein by reference.

Multi-component fibers may have any fiber diameter, the average diameter is 2 to 100 microns, preferably 3 to 60 microns, more preferably 5 to 20 microns, and may be continuous, random, or staple fiber. The multi-component fiber may be crimped on non-crimped.

Methods for making multi-component fibers are well known and need not be described here in detail. To form multi-component fibers, generally, the method includes feeding first and second molten mixtures as separate liquid streams to at least one orifice to form at least one multi-component molten filament comprised of first and second thermoplastic components while applying a gaseous stream to attenuate the extruded filaments; and collecting and cooling the filaments to a temperature below the melting temperature of the filament to solidify the multi-component fibers and thereby form a nonwoven fiber web.

In some exemplary embodiments, multi-component fibers exhibit an axial cross-sectional structure selected from the group consisting of a plurality of alternating layers of water-sensitive and non-water-sensitive thermoplastic polymer components, a plurality of alternating pie wedges of water-sensitive and non-water-sensitive thermoplastic polymer components, and a core/sheath structure wherein a water-sensitive thermoplastic polymer component makes up substantially all of the sheath and a non-water-sensitive thermoplastic polymer component comprises the fiber core. In some exemplary embodiments, applying a gaseous stream to at least one filament to attenuate the at least one filament to form a plurality of discrete, discontinuous, multi-component fibers is accomplished using a process selected from melt-blowing, gas jet fibrillation, and combinations thereof.

In some such exemplary embodiments, the process further includes at least one of addition of a plurality of staple fibers to the plurality of discrete, discontinuous, multi-component fibers, or addition of a plurality of particulates to the plurality of discrete, discontinuous, multi-component fibers. In further such exemplary embodiments, the process further includes collecting the plurality of discrete, discontinuous, multi-component fibers as the nonwoven fiber web on a collector. In some such embodiments, the process further includes processing the collected nonwoven fiber web using a process selected from autogenous bonding, through-air bonding, electret charging, embossing, needle-tacking, or a combination thereof.

A number of processes may be used for producing discrete multi-component fibers. Suitable processes and apparatus for producing discrete multi-component fibers include those described in U.S. Pat. No. 5,698,322 (Tsai et al), U.S. Pat. No. 7,008,207 B2 (Bansal et al.), and U.S. Pat. No. 8,926,877 B2 (Melik et al.). Particularly useful apparatus and methods, more particularly feed blocks for feeding multiple molten polymer streams to the die orifice(s) for producing discrete multi-component melt-blown fibers, are disclosed in U.S. Pat. No. 5,207,970 (Joseph et al.); U.S. Pat. No. 5,258,220 (Joseph et al.); U.S. Pat. No. 5,238,733 (Joseph et al.); and U.S. Pat. No. 5,232,770 (Joseph et al.), each incorporated herein by reference in its entirety.

To impart integrity and strength to the reinforced fiber web, the first and second fiber webs are entangled through the reinforcing mesh. Any suitable method may be used, but needle-tacking is generally a preferred technique. In the needle-tacking (also known as needle-punching) process, needles fitted with barbs (pushers and pullers) are rapidly punched into or through the reinforced fiber web thereby causing mechanical entanglement. Selection of effective needle-tacking conditions is within the capability of those having ordinary skill in the art. In some embodiments, hydroentanglement may be useful to entangle the first and second fiber webs.

After entangling of the first and second fiber webs, the reinforced fiber web may optionally be further processed to increase its integrity by a method such as, for example, hot calendering, oven bonding, and/or binder coating.

In some embodiments, the reinforced fiber web may have a basis weight of 50 to 600 grams per square meter (gsm), preferably 100 to 500 gsm, and more preferably 200 to 400 gsm, although other basis weights may also be used.

Referring now to FIG. 3, wound dressing material 300 comprises reinforced fiber web 100 having first and second opposed major sides (102, 104). First wound-contact scrim 320*a* comprises water-sensitive fibers comprising a first copolymer divalent hydroxyethylene monomer units and divalent dihydroxybutylene monomer units. First antimicrobial layer 330*a* is sandwiched between first major side 102 of reinforced fiber web 100 and first wound-contact scrim 320*a*. Optional second wound-contact scrim 320*b* comprises second water-soluble fibers comprising a second copolymer comprising divalent hydroxyethylene monomer units and divalent dihydroxybutylene monomer units. Optional second antimicrobial layer 330*b* is sandwiched between second major side 104 of reinforced fiber web 100 and optional second wound-contact scrim 320*b*.

The first and optional second wound-contact scrims may be the same or different. They comprise water-sensitive fibers that comprise first and optionally second copolymers (which may be the same or different), each respective copolymer comprising divalent hydroxyethylene monomeric units (i.e.,

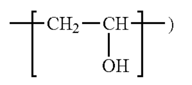

and divalent dihydroxybutylene monomer units. In preferred embodiments, the divalent dihydroxybutylene monomer units comprise 3,4-dihydroxybutan-1,2-diyl monomer units (i.e.,

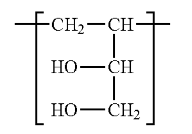

monomer units). Optionally, but typically, the copolymer furthers comprise acetoxyethylene divalent monomeric units (i.e., (i.e.,

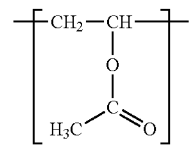

monomer units). The copolymer may be obtained by copolymerization of vinyl acetate and 3,4-dihydroxy-1-butene followed by partial or complete saponification of the acetoxy groups to form hydroxyl groups.

Alternatively, in place of 3,4-dihydroxy-1-butene, a carbonate such as

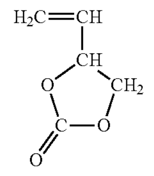

can also be used. After copolymerization, this carbonate may be hydrolyzed simultaneously with saponification of the acetate groups. In another embodiment, in place of 3,4-dihydroxy-1-butene, an acetal or ketal having the formula:

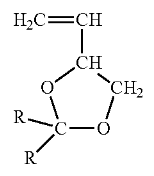

where each R is independently hydrogen or alkyl (e.g., methyl or ethyl). After copolymerization, this carbonate may be hydrolyzed simultaneously with saponification of the acetate groups, or separately. The copolymer can be made according to known methods or obtained from a commercial supplier, for example.

Commercially available copolymers may include those available under the trade designation Nichigo G-Polymer (Nippon Gohsei Synthetic Chemical Industry, Osaka, Japan), a highly amorphous polyvinyl alcohol, that is believed to have divalent monomer units of hydroxyethylene, 3,4-dihydroxybutan-1,2-diyl, and optionally acetoxyethylene. Nippon Gohsei also refers to Nichigo G-Polymer by the chemical name butenediol vinyl alcohol (BVOH). Exemplary materials include Nichigo G-Polymer grades AZF8035W, OKS-1024, OKS-8041, OKS-8089, OKS-8118, OKS-6026, OKS-1011, OKS-8049, OKS-1028, OKS-1027, OKS-1109, OKS-1081, and OKS-1083. These copolymers are believed to have a saponification degree of 80 to 97.9 mole percent, and further contain an alkylene oxide adduct of a polyvalent alcohol containing 5 to 9 moles of an alkylene oxide per mole of the polyvalent alcohol. These materials have melt-processing properties that are suitable for forming melt-blown and spunbond webs.

In some embodiments, the first and/or second water soluble fibers comprises three-layered fibers that an inner polymer layer (e.g., a polyurethane layer) sandwiched between two layers of the copolymer(s) described hereinbefore.

The first and optional second wound-contact scrims may contain secondary fibers in addition to the copolymer fibers. Suitable secondary fiber may include all fibers listed for the reinforced fiber web hereinbefore. Preferred secondary fibers include fibers comprising polyvinyl alcohol(s), carboxymethyl cellulose, rayon, cotton, cellulose acetate, hydrophilic thermoplastic polyurethane(s), chitosan, polyacrylic acid, sulfonated cellulose, cellulose ethyl sulfonate, alginate, or any combination thereof.

Methods of forming the wound-contact scrim(s) will depend on the type of fiber web formed, but will be well-known to those of skill in the textile arts. Suitable methods may include airlaying and/or carding of staple fibers followed by needle-tacking to densify and strengthen the fiber web; melt-blown; spunbond; and wet-laid processes.

In some embodiments, nonwoven fiber webs (e.g., the wound-contact scrim(s) may be made by air-laying of staple fibers. Air-laid nonwoven fiber webs may be prepared using equipment such as, for example, that available as a RANDO WEBBER from Rando Machine Company of Macedon, New York. In some embodiments, a type of air-laying may be used that is termed gravity-laying, as described e.g., in U.S. Pat. Application Publication 2011/0247839 (Lalouch). Nonwoven staple fiber webs may be densified and strengthened, for example, by techniques such as crosslapping, stitchbonding, needle-tacking, chemical bonding, and/or thermal bonding.

Melt-blowing methods are well-known in the art. As used herein, the term "melt-blowing" refers to a process in which fibers are formed by extruding a molten thermoplastic material through a plurality of fine, usually circular, die capillaries into a high velocity gas (e.g., air) stream which attenuates the molten thermoplastic material and forms fibers, which can be to microfiber diameter, such as less than 10 microns in diameter. Thereafter, the melt-blown fibers are carried by the gas stream and are deposited on a collecting surface to form a web of random melt-blown fibers. Such a process is disclosed, for example, in U.S. Pat. No. 3,849,241 (Butin et al.); U.S. Pat. No. 4,307,143 (Meitner et al.); and U.S. Pat. No. 4,707,398 (Wisneski et al.).

Fibers in the wound-contact scrims may be staple and/or continuous, preferably at least substantially continuous. For example, the first and/or optional second wound-contact scrims may comprise a meltblown fiber web or a spunbond fiber web. Fibers in the wound-contact scrims may have any average diameter and/or length, preferably from 2 to 200 microns and more preferably 2 to 100 microns.

The wound-contact scrim may have any basis weight, but in many embodiments, it is preferably in the range of 5 to 150 gsm, more preferably 10 to 100 gsm, and more preferably 10 to 75 gsm. Optionally, wound-contact scrims may further comprise at least one of addition of a plurality of staple fibers or addition of particulates. Suitable methods are described in U.S. Pat. No. 4,118,531 (Hauser), U.S. Pat. No. 6,872,3115 (Koslow), and U.S. Pat. No. 6,494,974 (Riddell); and in U.S. Pat. Appl. Publ. Nos. 2005/0266760 (Chhabra et al.), 2005/0287891 (Park), and 2006/0096911 (Bret' et al.). In other exemplary embodiments, the optional particulates may be added to a nonwoven fiber stream by air laying a fiber web, adding particulates to the fiber web (e.g., by passing the web through a fluidized bed of particulates), optionally with post heating of the particulate-loaded web to bond the particulates to the fibers.

Blends of fibers with and without resistance to exudate and/or water swellability/solubility can also be used for the reinforced fiber web and/or the first and/or optional second wound-contact scrims.

The antimicrobial layers provide effective topical antimicrobial activity and thereby treat and/or prevent a wide variety of afflictions. For example, they can be used in the treatment and/or prevention of afflictions that are caused, or aggravated by, microorganisms (e.g., Gram positive bacteria, Gram negative bacteria, fungi, protozoa, *mycoplasma*, yeast, viruses, and even lipid-enveloped viruses) on skin. Particularly relevant organisms that cause or aggravate such afflictions include *Staphylococcus* spp., *Streptococcus* spp., *Pseudomonas* spp., *Enterococcus* spp., and *Escherichia* spp., bacteria, as well as herpes virus, *Aspergillus* spp., *Fusarium* spp., *Candida* spp., as well as combinations thereof. Particularly virulent organisms include *Staphylococcus aureus* (including resistant strains such as Methicillin Resistant *Staphylococcus aureus* (MRSA), *Staphylococcus epidermidis, Streptococcus pneumoniae, Enterococcus faecalis*, Vancomycin Resistant *Enterococcus* (VRE), *Pseudomonas aeruginosa, Escherichia coli, Aspergillus niger, Aspergillus fumigatus, Aspergillus clavatus, Fusarium solani, Fusarium oxysporum, Fusarium chlamydosporum, Candida albicans, Candida glabrata, Candida krusei*, and combinations thereof.

In some embodiments, the antimicrobial layers may be a surface coating (e.g., a paste or gel) on either or both of the reinforced fiber web or a wound-contact scrim or it may be a freestanding layer (e.g., a film).

In some embodiments, antimicrobial layers, when provided as a free thin film (i.e., not as a coating on a substrate) have a basis weight in the range of 20 to 700 gsm, more preferably in the range of 75 to 600 gsm, and more preferably in the range of 100 to 500 gsm, are typically flexible and can be deformed without breaking, shattering, or flaking of the antimicrobial layer.

Each antimicrobial layer comprises at least one antimicrobial compound. Exemplary antimicrobial compounds include antibiotics (e.g., amoxicillin, bacitracin zinc, doxycycline, cephalexin, ciprofloxacin, clindamycin, metronidazole, azithromycin, sulfamethoxazole, trimethoprim, or levofloxacin), and antiseptics such as chlorhexidine and its salts (e.g., chlorhexidine digluconate and chlorhexidine diacetate), antimicrobial lipids, phenolic antiseptics, cationic antiseptics, iodine and/or an iodophor, peroxide antiseptics, antimicrobial natural oils, alkane-1,2-diols having 6 to 12 carbon atoms, silver, silver salts and complexes, silver oxide, copper, copper salts, and combinations thereof. Preferred antimicrobial compounds include antimicrobial quaternary amine compounds (e.g., benzalkonium chloride) and salts thereof, cationic surfactants (e.g., cetylpyridinium chloride or cetyltrimethylammonium bromide), polycationic compounds such as octenidine or a salt thereof, biguanide compounds (e.g., chlorhexidine, polyhexamethylenebiguanide (PHMB) or a salt thereof, 1,2-organic diols having 6 to 12 carbon atoms (e.g., 1,2-octanediol), antimicrobial fatty acid monoester compounds, and combinations thereof.

Wound dressing materials according to the present disclosure may have broad-spectrum antimicrobial activity. However, the wound dressing materials are typically sterilized; for example, by sterilized by a variety of industry standard techniques. For example, it may be preferred to sterilize the wound dressing materials in their final packaged form using electron beam. It may also be possible to sterilize the sample by gamma radiation, nitrogen dioxide sterilization and/or heat. Other forms of sterilization may also be used. It may also be suitable to include preservatives in the formulation to prevent growth of certain organisms. Suitable preservatives include industry standard compounds such as parabens (e.g., methylparaben, ethylparaben, propylparaben, isopropylparaben, or isobutylparaben); 2 bromo-2 nitro-1,3-diol; 5 bromo-5-nitro-1,3-dioxane, chlorbutanol, diazolidinyl urea; iodopropyl butyl carbamate, phenoxyethanol, halogenated cresols, methylchloroisothiazolinone; and combinations thereof.

Many preferred antimicrobial layers comprise an effective amount of a polycarboxylic acid chelator compound, alone or in combination with any of the foregoing antimicrobial compounds. The amount is effective to prevent growth of a microorganism and/or to kill microorganisms on a surface to which the composition is contacted.

In certain embodiments, the polycarboxylic acid chelator compound, whether aliphatic, aromatic, or a combination thereof, comprises at least two carboxylic acid groups. In certain embodiments, the polycarboxylic acid chelator compound, whether aliphatic, aromatic or a combination thereof, comprises at least three carboxylic acid groups. In certain embodiments, the polycarboxylic acid chelator compound, whether aliphatic or aromatic, comprises at least four carboxylic acid groups.

Polycarboxylic acid-containing chelator compounds suitable for use in antimicrobial layer include aliphatic polycarboxylic acids, aromatic polycarboxylic acids, compounds with both one or more aliphatic carboxylic acids and one or more aromatic carboxylic acids, salts thereof, and combinations of the foregoing. Nonlimiting examples of suitable polycarboxylic acid-containing chelator compounds include citric acid, glutaric acid, glutamic acid, maleic acid, succinic acid, tartaric acid, malic acid, ethylenediaminetetraacetic acid, phthalic acid, trimesic acid, and pyromellitic acid.

Preferred salts include those formed from monovalent inorganic bases and include cations such as $K^+$, $Na^+$, $Li^+$, and $Ag^+$, and combinations thereof. In some compositions polyvalent bases may be appropriate and include cations such as $Ca^{2+}$, $Mg^{2+}$, $Zn^{2+}$, Alternatively, the salt of the polycarboxylic acid may be formed using an organic base such as a primary, secondary, tertiary, or quaternary amine.

In many embodiments, the polycarboxylic acid-comprising chelator compound may be present in the antimicrobial layer at relatively high concentrations (on a weight basis) while the composition remains surprisingly non-frangible. The minimum effective amount of chelator compound in the antimicrobial layer is related to the number of carboxyl groups in the chelator compound. For example, succinic acid (with two carboxyl groups) is generally more efficacious than glutamic acid having the same number of carboxylic acid groups since in glutamic acid carboxyl group forms a zwitterion with an amino group.

Mucic acid is another example with 2 carboxyl groups. Mucic acid is not as efficacious as succinic acid since the carboxyl groups are further apart and sterically hindered. In certain embodiments, efficacy of the composition can be improved by using thicker (greater basis weight) antimicrobial layers. Efficacy may depend on the amount of acid in the antimicrobial layer as well as the total amount (mass) of the antimicrobial layer. Thus, in some embodiments, the chelator compound comprises at least about 5, 10, 15, 20, 25, 30, 35, 40, 45, 50, 55, or even at least 60 percent by weight of an essentially solvent-free antimicrobial layer. The term "essentially solvent-free" is understood to mean that the antimicrobial layer has been processed to remove most of the solvent (e.g., water and/or organic solvent) or has been processed in such a way that no solvent (e.g., water and/or organic solvent) was required. This is generally the article for sale, e.g., before it has been applied to a patient. Generally, solvents are relatively volatile compounds having a boiling point at one atmosphere pressure of less than 150° C. Solvent may be used to process (e.g., coat or film-form) the antimicrobial layer, but is preferably substantially removed to produce the final article for sale. For example, certain precursor compositions used to form the antimicrobial layer are first combined with water as a vehicle to form a solution, emulsion, or dispersion. These precursor compositions are coated and dried on a substrate (e.g., a release liner, the reinforced fiber web, and/or the wound-contact scrim(s)) such that the water content of the antimicrobial layer is less than 10 percent by weight, preferably less than 5 percent by weight, and more preferably less than 2 percent by weight.

In some embodiments, the chelator compound comprises up to about 15, 20, 25, 30, 35, 40, 45, 50, 55, or even up to about 60 percent by weight of the essentially dry antimicrobial layer on a weight basis.

In certain embodiments, wherein the polycarboxylic acid-comprising chelator compound comprises two aliphatic carboxylic acid groups (e.g., succinic acid), the chelator compound comprises at least about 10 percent by weight of the essentially dry antimicrobial layer on a weight basis. In certain embodiments, wherein the polycarboxylic acid-comprising chelator compound comprises three aliphatic carboxylic acid groups (e.g., citric acid), the chelator compound comprises at least about 10 percent by weight of the essentially dry antimicrobial layer on a weight basis. In certain embodiments, wherein the polycarboxylic acid-comprising chelator compound comprises four aliphatic carboxylic acid groups (e.g., ethylenediaminetetraacetic acid), the chelator compound comprises at least about 5 percent by weight of the essentially dry antimicrobial layer on a weight basis.

When preparing antimicrobial layers of the present disclosure, the polycarboxylic acid-containing chelator compound may be dissolved and/or dispersed in a water-soluble plasticizer component and optionally a solvent such as water. The plasticizer component has a boiling point greater than 105° C. and has a molecular weight of less than 5000 daltons. Preferably, the plasticizer component is a liquid at 23° C. Typically, but not necessarily, the plasticizer component is the most abundant solvent in the antimicrobial layer in which the polycarboxylic acid-containing chelator compound is dissolved and/or dispersed. In certain embodiments wherein water is used to prepare the antimicrobial layer, substantially all of the water is subsequently removed (e.g., after the antimicrobial layer has been coated onto a substrate).

In certain embodiments, the chelator compound comprises an aliphatic and/or aromatic polycarboxylic acid, in which two or more of the carboxylic groups are available for chelation without any zwitterionic interaction. Although potential zwitterionic interactions (e.g., such as in L-glutamic acid) may decrease antimicrobial efficacy relative to similar compounds (e.g., glutaric acid, succinic acid) that do not comprise α-amino groups, such zwitterionic compounds also exhibit antimicrobial activity. In addition, two or more carboxylic acid groups in the polycarboxylic acid-containing chelator compounds should be disposed in the chelator compound in sufficient proximity to each other or the compound should be capable of folding/conforming to bring the carboxylic acids sufficiently close to facilitate chelation of metal ions.

In certain embodiments, the chelator compound comprises an aliphatic polycarboxylic acid or a salt thereof, an aromatic polycarboxylic acid or a salt thereof, or a combination thereof. In certain embodiments, the chelator compound comprises an aliphatic portion. In certain embodiments, the chelator compound comprises an aliphatic portion. The carboxylic acids may be disposed on the aliphatic portion and/or on the aromatic portion. Nonlimiting examples of chelator compounds that comprise an aliphatic portion with a carboxylic acid group disposed thereon and an aromatic portion with a carboxylic acid group disposed therein include 3-(2-carboxyphenyl)propionic acid, 3-(4-carboxyphenyl)propionic acid, and 4[(2-carboxyphenyl)amino]benzoic acid.

In certain embodiments, efficacy of the antimicrobial layer can be improved by depositing a higher amount of dried antimicrobial layer. Efficacy is dependent on concentration of chelator compound in the antimicrobial layer as well as total amount of the antimicrobial layer.

The antimicrobial layer may contain plasticizer. Suitable plasticizers may include, for example, glycerol, a polyglycerol having 2-20 glycerin units, polyglycerols partially esterified with $C_1$-$C_{18}$ alkylcarboxylic acids having at least two free hydroxyl groups (e.g., hexaglycerol monolaurate, decaglycerol monolaurate, polyglyceryl-6 caprate, polyglyceryl-4 oleate, polyglyceryl-10 trilaurate and the like), polyethylene oxide, polyethylene glycol, polyethylene glycols initiated by any of the glycols discussed herein such as polyethylene glycol glyceryl ether, propylene glycol, dipropylene glycol, tripropylene glycol, 2-methyl-1,3-propanediol, sorbitol, dimethylisosorbide, pentaerythritol, trimethylolpropane, ditrimethylolpropane, a random ethylene oxide/propylene oxide (EO/PO) copolymer or oligomer, a block EO/PO copolymer or oligomer, and combinations thereof.

Plasticizer may be present in the antimicrobial layer at relatively high concentrations (on a weight basis). In some embodiments, plasticizer comprises at least about 10 percent by weight of the antimicrobial layer. In some embodiments, plasticizer comprises at least about 10, 15, 20, 25, 30, 35, 40, 45, 50, 55, 60, 65, 70, or even at least 75 percent by weight of the antimicrobial layer. In certain embodiments, the plasticizer component can act as a humectant. Advantageously, this can maintain a moist environment in a wound to help promote healing of wound tissue.

Advantageously, the relatively high concentration of plasticizer and/or water-soluble or water-dispersible polymer in the antimicrobial layer can function as a controlled-release modulator that facilitates delivery of the antimicrobial(s) over an extended period of time. In some embodiments, the plasticizer component can also function as an antimicrobial component.

Antimicrobial layers according to the present disclosure are preferably solid at 25° C. In certain embodiments, the antimicrobial layer may comprise a solvent having a normal boiling point of less than or equal to 100° C. Nonlimiting examples of such solvents include water and lower ($C_2$-$C_5$) alcohols. Preferably, before use, the antimicrobial layer comprises very little solvent (e.g., less than or equal to about 10 percent by weight) having a normal boiling point of less than or equal to 100° C. In some embodiments, the antimicrobial layer comprises less than 5 percent by weight, less than 4 percent by weight, less than 3 percent by weight, less than 2 percent by weight, or even less than 1 percent by weight (by weight) of a solvent having a normal boiling point of less than or equal to 100° C. In certain embodiments, the antimicrobial layer may be substantially free (before use) of such solvents or any compounds having a normal boiling point of less than 100° C.

In many preferred embodiments, the antimicrobial layer(s) comprise a water-soluble or water-dispersible polymer as a binder. The water-soluble or water-dispersible polymer has a Tg greater than or equal to 20° C. In use, the polymer can function to form the antimicrobial layer into a cohesive shape such as a film while also absorbing wound exudate and to maintain a moist environment that can facilitate healing of the tissue at a wound site.

Exemplary water-soluble and/or water-dispersible polymers that are suitable for use in a antimicrobial layer according to the present disclosure include polyvinylpyrrolidone; polyvinyl alcohol; copolymers of vinyl alcohol; polybutylenediol; polysaccharides (e.g., starch); guar gum; locust bean gum; carrageenan; hyaluronic acid; agar; alginate; tragacanth; gum arabic; gum karraya; gellan; xanthan gum; hydroxyethylated, hydroxypropylated, and/or cationic derivatives of the foregoing; modified cellulose polymers (e.g., hydroxyethylcellulose, hydroxypropyl methylcellulose, carboxymethylcellulose, or cationic cellulose such as polyquaterium 4); copolymers of polyvinylpyrrolidone and vinyl acetate; water-soluble and water-swellable polyacrylates (e.g., based on hydroxyethyl (meth)acrylate, hydroxypropyl (meth)acrylate, (meth)acrylic acid, (meth)acrylamide, PEG (meth)acrylates, methyl (meth)acrylate), and combinations thereof. As used herein the term "(meth)acryl" refers to acryl and/or methacryl. In certain embodiments, the water-soluble or water-dispersible polymers can comprise a polyquaternium polymer.

In some embodiments, the water-soluble or water-dispersible polymer comprises at least about 5 percent by weight of the antimicrobial layer. In some embodiments, the water-soluble or water-dispersible polymer comprises up to about 65 percent by weight of the antimicrobial layer.

The antimicrobial layers according to the present disclosure preferably adhere well to the reinforced fiber web and the wound-contact scrim(s).

When contacting a wound site, the antimicrobial layer and/or articles of the present disclosure are hydrated by the tissue fluids and wound exudate Antimicrobial layers according to the present disclosure comprise polycarboxylic acid chelator compounds that, in an aqueous environment, have antimicrobial properties at an acidic pH. Thus, antimicrobial layers of the present disclosure comprise appropriate quantities of acidic components (e.g., the free acid of the polycarboxylic acid chelator compound) and basic components (e.g., NaOH or a salt of a polycarboxylic acid chelator compound) such that the antimicrobial layer, when mixed well with deionized water at a 1:9 mass ratio, forms an aqueous mixture having a pH of about 2.5 to 5.5. In certain embodiments, the pH of the resulting aqueous mixture is at least 2.5, 3.0, 3.5, 4.0, 4.5, 5.0, or even at least 5.5.

A variety of other ingredients may be added to the antimicrobial layers according to the present disclosure for desired effect. These include, but are not limited to, surfactants, skin emollients and humectants such as, for example, those described in U.S. Pat. No. 5,951,993 (Scholz et al.), fragrances, colorants, and/or tackifiers.

Optionally a flexible adhesive barrier film is adhered to and proximate to the second major side of the reinforced fiber web. Referring now to FIG. 4, wound dressing material 400 comprises reinforced fiber web 100 having first and second opposed major sides (102, 104). First wound-contact scrim 420*a* comprises copolymer fibers comprising divalent hydroxyethylene monomer units and divalent dihydroxybutylene monomer units. First antimicrobial layer 430*a* is sandwiched between first major side 102 of reinforced fiber web 100 and first wound-contact scrim 420*a*. Flexible adhesive barrier film 440 is adhered to and proximate to second major side 104 of reinforced fiber web 100. In the particular embodiment shown, flexible adhesive barrier film 440 extends beyond the periphery of the other components such as the first wound contact scrim 420*a*, first antimicrobial layer 430*a*, and reinforced fiber web 100 so that it may stick to the skin surrounding the wound, however this is not a requirement. In this embodiment, the exposed adhesive side of the adhesive barrier film may be protected by a disposable protective releasable liner 460.

Commercially available suitable flexible adhesive barrier films are marketed by 3M Company under the trade designation TEGADERM (e.g., 3M TEGADERM Transparent Film Roll), by Johnson & Johnson Company, New Brunswick, New Jersey under the trade designation BIOCLUSIVE, and by T. J. Smith & Nephew, Hull, England under the trade designation OP-SITE.

Wound dressing materials according to the present disclosure may have any basis weight, thickness, porosity, and/or density unless otherwise specified. In some embodiments, the wound dressing materials comprise a lofty open nonwoven fiber web.

Wound dressing materials according to the present disclosure may have any desired thickness. In many embodiments, the thickness is in the range of 0.5 to 6 mm, more preferably 0.75 to 5 mm, and more preferably 1 to 4 mm. In many embodiments, the basis weight is in the range of 100 to 1000 gsm, more preferably 150 to 900 gsm, and more preferably 200 to 800 gsm. Likewise, the reinforced fiber web may have any basis weight, but in many embodiments, it is preferably in the range of 20 to 500 gsm, more preferably 50 to 400 gsm, and more preferably 75 to 300 gsm.

The wound dressing material may be provided in roll form, or it may be converted into sheets or bandages (optionally further comprising a peripheral supporting frame).

Preferably, to maintain a low relative humidity, the wound dressing material should be packaged in a package with a low moisture vapor transmission rate (MVTR) such as, for example, a Techni-Pouch package (Technipaq, Inc., Crystal Lake, Illinois) with a PET/Aluminum Foil/LLDPE material construction.

Wound dressing materials according to the present disclosure can be made by any suitable method, including, for example, sequential or simultaneously pressure and/or heat lamination of the wound-contact scrim(s), antimicrobial layer(s), fiber web, and optional flexible adhesive barrier film. In some embodiments, the antimicrobial layers may be coated (e.g., spray coated, roll coated, curtain coated, or gravure coated), typically with an associated drying step, onto either or both of the wound-contact scrim(s) and the reinforced fiber web. Such manufacturing techniques will be apparent to those of ordinary skill in the art.

Wound dressing materials according to the present disclosure are useful, for example, for covering a wound. Typically, exposed surface of the wound is cleaned and/or treated with antiseptic (if necessary) and then contacted with the first wound-contact scrim of the wound dressing material, although this is not a requirement. In some embodiments, the wound dressing material can be covered with a secondary wound dressing.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Example 1

A blown microfiber (BMF) web was made using a melt blowing process similar to that described in V. A. Wente, "Superfine Thermoplastic Fibers" in Industrial Engineering Chemistry, Vol. 48, pages 1342 et seq. (1956). The extruder feeding molten polymer to the melt-blowing die was a STEER 20-mm twin screw extruder commercially available from Steer America (Uniontown, Ohio), equipped with two weight loss feeders to control the feeding of the polymer resins to the extruder barrel and a melt pump to control the polymer melt flow to a melt-blowing die. The die had a plurality of circular smooth surfaced orifices (10 orifices/cm) with a 5:1 diameter ratio.

The reinforced fiber web example discussed below were made using an apparatus equipped with a multi-layer feed block configured to obtain multi-component blown microfibers that exhibit an axial cross-sectional structure as generally described in FIG. 2 are described in, e.g., U.S. Pat. No. 5,232,770 (Joseph et al.), when the fiber is viewed in axial cross-section, consisting of three layers.

A BMF web was made with each fiber having 3 layers. The inner layer of the fiber was made of TECOPHILIC TPU TG2000 hydrophilic thermoplastic polyurethane obtained from the Lubrizol Corporation (Wickliffe, Ohio) and the outer layers were made using a blend of Dow DNDA 1081 Linear low-density polyethylene (LLDPE) obtained from the Dow Chemical Company (Midland, Michigan) and UNITHOX 490 ethoxylate nonionic emulsifier obtained from the Baker Hughes Company (Houston, Texas). The two extruders were kept at the same temperature at 210° C. to deliver the melt stream to the BMF die (maintained at 210° C.). The gear pumps were adjusted to obtain a 75/25 ratio of TECOPHILIC TPU TG2000/(LLDPE+6% UNITHOX 490 ethoxylate blend). The gear pump was adjusted so that a 1.0 lb/hour/inch die width (0.178 kg/hour/cm die width) polymer throughput rate was maintained at the die. The primary air temperature of the air knives adjacent to the die orifices was maintained at approximately 325° C.

The BMF fibers were directed to a drum collector and staple fibers were dispensed in between the BMF die and drum collector. The staple fibers were a combination of polyethylene terephthalate (PET) staple fibers and melty fibers in the weight ratio 80/20. The PET fibers were crimped with a 38.1 mm length and 3.3 dtex, and were obtained from Invista (Wichita, Kansas). The melty fibers were made from Tairilin Polyester fiber Type LML41 from NanYa Plastics (New Taipei City, Taiwan) and had a fiber diameter of 4 denier and a length of 2 inches (5.1 cm). Sufficient staple fibers were dispensed so as to constitute 30% by weight of the resultant fiber web. The resultant fiber web was collected at a BMF die to collector distance of 53.3 cm and a collection rate of 2.7 meters/minute. The web had a basis weight of approximately 150 gsm and a fiber diameter range of 5-30 micrometers.

The web was subjected to heat treatment to further increase the mechanical properties. The web was placed on a porous belt and sent through a heating apparatus set at 127° C. in which hot air was drawn through the thickness of the collected fibers from top to bottom. Table 1, below reports the composition of fiber webs prepared in Example 1.

TABLE 1

| EXAMPLE | 3-LAYER FIBER, 70 wt. % of fiber web Middle layer wt. % TECOPHILIC TPU TG2000 | Outer Layers wt. % (94% LLDPE1081 + 6% UNITHOX 490) | 80% PET + 20% Melty, total wt. % in fiber web | NOMINAL BASIS WEIGHT OF THE RESULTING NONWOVEN WEB, $g/m^2$ |
|---|---|---|---|---|
| 1 | 75 | 25 | 30 | 150 |

Example 2

Two layers of the fiber web described in Example 1 (before oven bonding) were needled together with a reinforcing mesh sandwiched in the middle. The reinforcing mesh was a utility mesh knit fabric made of 100% polyester obtained from JoAnn fabrics (Utility 194-8439, Hudson, Ohio). The knit pattern had a regular array of openings that occupied a majority of the mesh surface area. The 3 layers were then needle-tacked using a conventional needle-tacking apparatus. The needle-tacking equipment was a DILO group (DILO-Typ DI-LOOM OD-1 6; Number: 9016/2001, Charlotte, North Carolina). The needle board had 10.4 needles/sq.in. needles (Foster Needle type 15×18×36×3 BA). The needles were punched at 565 strokes per minute through the full thickness of the web to generate physical entanglements making an integral web. The web was fed at 10 ft/min (3.0 m/min) to the needler at draw ratio of 11%. The resulting web was collected at 11.1 ft/min (3.4 m/min) and had a basis weight of 360 grams per square meter.

Example 3

Example 2 was repeated, except that the reinforcing mesh was a 100% Polyester apparel interfacing—specialty 180—Knit-N-Stable (Pellon products—15654049) from Pellon Consumer Products, Clearwater, Florida).

The samples described in examples above were compared with the following wound dressings. Aquacel Ag Extra is a commercially available water-gelling nonwoven wound dressing that is stitchbonded for extra strength marketed by Convatec, Berkshire, United Kingdom. SFN-CMC 160 gsm is a commercially available modified cellulose water-gelling nonwoven wound dressing marketed by Specialty Fibers and Materials (Coventry, United Kingdom).

Tensile tests were performed using Instron Model number 5544, Instron (Canton, Massachusetts), wherein MD refers to the machine Direction and CD refers to the crossweb direction.

Tables 2 to 4, below report tensile properties of reinforced fiber webs under various conditions. The tensile properties of webs in the Examples were measured by pulling to failure a 1 inch (2.54 cm) by 4 inch (10.2 cm) specimen. The gauge length was 2 inches (5.1 cm), and the cross-head speed was 10 in/min (25.4 cm/min). The Maximum Tensile Load was determined in the machine direction and cross direction of the nonwoven fibrous web.

TABLE 2

| SPECIMEN | DRY MD, pounds-force | DRY CD pounds-force |
|---|---|---|
| Aquacel Ag Extra | 10.1 | 5.23 |
| SFN-CMC 160 gsm | 16.6 | 6.26 |
| Example 1 | 1.64 | 2.02 |
| Example 3 | 23.8 | 18.2 |
| Example 2 | 42.7 | 14.8 |

TABLE 3

| SPECIMEN | SOAKED IN WATER FOR 5 MINUTES MD, pounds-force | SOAKED IN WATER FOR 5 MINUTES CD pounds-force |
|---|---|---|
| Aquacel Ag Extra | 3.01 | 1 |
| SFN-CMC 160 gsm | 2.36 | 0.98 |
| Example 1 | 0.52 | 0.51 |
| Example 3 | 18.63 | 13.34 |
| Example 2 | 17.88 | 12.11 |

TABLE 4

| TIME SUBMERGED IN WATER BATH, hrs | EXAMPLE 2 MD, pounds-force | EXAMPLE 2 CD pounds-force |
|---|---|---|
| 0 | 41 | 14.75 |
| 0.08 | 26 | 12 |
| 0.5 | 30 | 10.5 |
| 24 | 26 | 11.5 |
| 48 | 25.75 | 13.5 |
| 144 | 30.5 | 11.5 |

Example 4

A multi-layer wound dressing article was assembled using the reinforced fiber web from Example 5, antimicrobial coating layers, and layers of butenediol vinyl alcohol (BVOH) nonwoven material. The components were layered in the construction reported in Table 5, below:

TABLE 5

| |
|---|
| BVOH nonwoven- 20 gsm |
| 4 antimicrobial coating layers - 400 gsm total, (4 × 100 gsm) |
| Reinforced fiber web of Example 2 |
| 4 antimicrobial coating layers - 400 gsm total, (4 × 100 gsm) |
| BVOH nonwoven - 20 gsm |

First, the antimicrobial layers were laminated one at a time to one side of the reinforced fiber web from Example 2 using hand pressure followed by removal of the liner on each antimicrobial layer as it was added. Then, the BVOH nonwoven layer was laminated to the antimicrobial layers using hand pressure. An identical procedure was used to the laminate the layers on the opposing side of the N-net core nonwoven layer. The final wound dressing article was trimmed to make a 4 in×4 in (10.2 cm×10.2 cm) wound dressing article.

Details concerning the method of making the BVOH fiber layer and the antimicrobial coating layers is described below.

Preparation of BVOH Nonwoven Layer:

A melt-blown (blown microfiber, BMF) nonwoven fiber web was made using Nichigo G-Polymer butanediol vinyl alcohol copolymer (BVOH) pellets (obtained as Nichigo G-Polymer OKS 8112) from the Mitsubishi Chemical Corporation, Tokyo, Japan). A conventional melt-blowing process was employed similar to that described in V. A. Wente, "Superfine Thermoplastic Fibers" in Industrial Engineering Chemistry, Vol. 48, pages 1342 et seq. (1956). The melt-blowing die had circular smooth surfaced orifices, spaced 10 to the centimeter, with a 5:1 length to diameter ratio. Molten (co)polymer was delivered to the die by a 20 mm twin screw extruder commercially available from SIEER Co., Union Town, Ohio. This extruder was equipped with two weight loss feeders to control the feeding of the (co)polymer resins to the extruder barrel, and a gear pump to control the (co)polymer melt flow to a die. The extruder temperature was at about 210° C. and it delivered the melt stream to the BMF die, which itself maintained at 210° C. The gear pump was adjusted so that 1.0 lb/hr/inch die width (0.178 kg/hr/cm die width) polymer throughput rate was maintained at the die. The primary air temperature of the air knives adjacent to the die orifices was maintained at approximately 325° C. This produced a web on a rotating collector spaced 10 cm from the die, the speed of the collector was 42.4 ft/min (12.9 m/min). The web had a basis weight of approximately 20 g/m 2 and was composed with the fiber diameter in the range of 5-25 micrometers.

Preparation of the Antimicrobial Composition:

Antimicrobial compositions were made in 100 g quantities according to the formula listed in Table 6. All of the ingredients except the L-PVPK60 was added to a MAX 100 cup (Flacktec Inc., Landrum, South Carolina) and mixed at 3500 rpm for 1 minute using a DAC 400 FVZ SpeedMixer instrument (Flacktec, Inc.). Subsequently, L-PVPK60 aqueous mixture was added to the cup and mixed for an additional minute at 3500 rpm.

TABLE 6

| COMPONENT | WEIGHT PERCENT | SOURCE |
|---|---|---|
| Glycerol | 24.44 | Cargill Corporation, Wayzata, Minnesota |
| Linear polyvinylpyrrolidone K60, 47% in water (L-PVPK60) | 64.01 | Ashland Incorporated, Covington, Kentucky |
| Benzalkonium chloride 50% (BAC) | 0.18 | Novo Nordisk Pharmatech, Koge, Denmark |
| Hydrolite 8 Capryl glycol | 0.70 | Symrise AG, Holzminden, Germany |
| Sterile water | 6.17 | Rocky Mountain Biologicals, Missoula, Montana |
| Sodium citrate | 2.57 | MilliporeSigma, St. Louis, Missouri |
| Citric acid monohydrate | 1.93 | MilliporeSigma |
| Total | 100.00 | |

Preparation of Antimicrobial Film/Layer Comprising the Composition

On the day composition was produced as described above, the viscous composition was knife-coated onto a release liner using a gap of 254 microns. The coating was dried at 80° C. for 10 minutes in a convection oven to dry the coating and to finally produce a coating with a basis weight of 100 g/m$^2$.

All cited references, patents, and patent applications in this application that are incorporated by reference, are incorporated in a consistent manner. In the event of inconsistencies or contradictions between portions of the incorporated references and this application, the information in this application shall control. The preceding description, given in order to enable one of ordinary skill in the art to practice the claimed disclosure, is not to be construed as limiting the scope of the disclosure, which is defined by the claims and all equivalents thereto.

What is claimed is:

1. A wound dressing material comprising:

a reinforced fiber web having first and second opposed major sides, wherein the reinforced fiber web comprises first and second fiber webs having a reinforcing mesh disposed between the first and second fiber webs, and wherein the first fiber web, the second fiber web, and the reinforcing mesh are bonded to one another by a combination of physical entanglement and thermal bonding;

a first wound-contact scrim comprising first water-sensitive fibers, wherein the first water-sensitive fibers comprise a first copolymer comprising divalent hydroxyethylene monomer units and divalent dihydroxybutylene monomer units; and a first antimicrobial layer disposed between the first major side of the reinforced fiber web and the first wound-contact scrim.

2. The wound dressing material of claim 1, wherein at least one of the first or second fiber webs comprises second water-sensitive fibers comprising hydrophilic aliphatic thermoplastic polyurethane.

3. The wound dressing material of claim 2, wherein the second water-sensitive fibers comprise multilayer fibers comprising top and bottom layers comprising polyethylene, and wherein a central layer comprising hydrophilic aliphatic thermoplastic polyurethane is disposed between the top and bottom layers.

4. The wound dressing material of claim 1, further comprising:

a second wound-contact scrim comprising second water-sensitive fibers, wherein the second water-sensitive fibers comprise a second copolymer comprising divalent hydroxyethylene monomer units and divalent dihydroxybutylene monomer units; and a second antimicrobial layer disposed between the second major side of the reinforced fiber web and the second wound-contact scrim.

5. The wound dressing material of claim 4, wherein the second water-sensitive fibers comprise multilayer fibers comprising top and bottom layers comprising polyethylene, and wherein a central layer comprising hydrophilic aliphatic thermoplastic polyurethane is disposed between the top and bottom layers.

6. The wound dressing material of claim 1, wherein the reinforcing mesh comprises a knit fabric having regularly spaced openings extending therethrough.

7. The wound dressing material of claim 1, wherein the first water-sensitive fibers have an average fiber diameter of 2 to 100 microns.

8. The wound dressing material of claim 1, wherein the first copolymer further comprises divalent acetoxyethylene monomer units.

9. The wound dressing material of claim 1, wherein the divalent dihydroxybutylene monomer units comprise divalent 3,4-dihydroxybutan-1,2-diyl monomer units.

10. The wound dressing material of claim 1, wherein the first wound-contact scrim is melt-blown or spunbonded.

11. The wound dressing material of claim 1, wherein at least one of the first fiber web or the second fiber web comprises meltblown fibers and at least one of the first fiber web or the second fiber web comprises staple fibers.

12. The wound dressing material of claim 1, wherein the first and second fiber webs are bonded together and to the reinforcing mesh by stitchbonding as the physical entanglement in combination with thermal bonding.

13. A reinforced fiber web having first and second opposed major sides, wherein the reinforced fiber web comprises first and second fiber webs having a reinforcing mesh disposed therebetween, wherein the first fiber web, second fiber web, and the reinforcing mesh are bonded to one another by a combination of physical entanglement and thermal bonding, and wherein at least one of the first and second fiber webs comprises water-sensitive fibers comprising hydrophilic aliphatic thermoplastic polyurethane.

14. The reinforced fiber web of claim 13, wherein the water-sensitive fibers comprise multilayer fibers comprising top and bottom layers comprising polyethylene, and wherein a central layer comprising hydrophilic aliphatic thermoplastic polyurethane is disposed between the top and bottom layers.

15. The reinforced fiber web of claim 13, wherein the reinforcing mesh comprises a knit fabric having regularly spaced openings.

16. The reinforced fiber web of claim 13, wherein at least one of the first fiber web or the second fiber web comprises meltblown fibers and staple fibers.

17. A method of forming a reinforced fiber web, the method comprising:

providing a first fiber web;

providing a second fiber web;

disposing a reinforcing mesh between the first and second fiber webs; and bonding the first fiber web, the second fiber web, and the reinforcing mesh together by a combination of physical entanglement and thermal bonding to form a unitary reinforced fiber web structure having first and second opposed major sides.

18. The method of claim 17, wherein the reinforced fiber web further comprises a wound-contact scrim comprising water-sensitive fibers and secondary fibers comprising at least one polymer selected from the group consisting of:

polyvinyl alcohol, carboxymethyl cellulose, rayon, cotton, cellulose acetate, thermoplastic polyurethane, chitosan, polyacrylic acid, sulfonated cellulose, alginate, cellulose ethyl sulfonate, polyethylene, polypropylene, polybutylene, poly(ether ether ketone), poly-4-methylpentene, polyethylene terephthalate, polyvinyl chloride, polymethyl methacrylate, polyacrylonitrile, a polyamide, a polyester, polystyrene, a styrenic block copolymer, a polyurethane comprising polyethers, a block copolymer of polyether, and polypropylene oxide.

19. The method of claim 17, further comprising:

disposing a first antimicrobial layer on the first major side of the reinforced fiber web, wherein the first antimicrobial layer comprises at least 10 percent by weight of a polycarboxylic acid chelator compound and at least 10 percent by weight of a plasticizer.

20. The method of claim 17, wherein the first and second fiber webs are bonded to the reinforcing mesh by stitchbonding as the physical entanglement in combination with thermal bonding.

* * * * *